United States Patent [19]

Ranger

[11] 4,179,932
[45] Dec. 25, 1979

[54] SUPPLY APPARATUS

[76] Inventor: Hubert O. Ranger, 1535 E. Goodrich La., Milwaukee, Wis. 53217

[21] Appl. No.: 905,317

[22] Filed: May 12, 1978

[51] Int. Cl.$^2$ .......................... B08B 5/00; G01N 1/14
[52] U.S. Cl. .................................................. 73/423 A
[58] Field of Search ............. 73/421 B, 423 A, 423 R

[56] References Cited

U.S. PATENT DOCUMENTS

| | | | |
|---|---|---|---|
| 3,252,327 | 5/1966 | Ferrari ................................ | 73/423 A |
| 3,252,330 | 5/1966 | Kling ................................... | 73/423 A |
| 3,266,322 | 8/1966 | Negersmith et al. ............... | 73/423 A |
| 3,282,651 | 11/1966 | Ferrari et al. ..................... | 73/423 A X |
| 3,795,149 | 3/1974 | Gillette et al. ..................... | 73/423 A |
| 3,836,329 | 9/1974 | Jordan ................................ | 73/423 A X |

*Primary Examiner*—Daniel M. Yasich

*Attorney, Agent, or Firm*—Francis J. Bouda

[57] ABSTRACT

A supply device for liquid analysis apparatus including a probe and a sample container, said probe and said container being relatively movable with respect to each other whereby liquid carried within the container may be removed by said probe when the probe is disposed within the container, said probe including a takeoff conduit with a valve disposed therein, rinse fluid supplied to said conduit through said valve, said valve preventing rinse fluid from entering said conduit when the sample is moving from said container through the probe, said rinse fluid flowing through said conduit and at least a portion thereof flowing out of said probe when said valve is opened, thereby cleansing the conduit and the probe.

1 Claim, 4 Drawing Figures

SUPPLY APPARATUS

BACKGROUND OF THE INVENTION

This invention relates to an improved method of sampling discrete segments of fluid, cleaning the system between the samples, and introducing the sample for further processing or direct measurement.

Samplers which draw fluids from cups, rinse the sampling system, conduct the sample to processing systems, and then sequentially repeat the process are known. Patents in this field include:

3,134,263 DeJong
3,230,776 Isreeli
3,251,229 Isreeli
3,804,593 Smythe
3,960,003 Beyer All of these previous devices disclose a probe moving into and out of a sample source, and then into and out of a rinse receptacle that furnishes rinse fluid to the probe. When the probe moves out of the rinse receptacle the cycle is repeated.

Such devices are cumbersome and expensive because they involve complicated apparatus for moving the probe into and out of the sample container and then swinging the probe laterally to move the probe into and out of the cleansing bath.

SUMMARY OF THE INVENTION

This invention relates to a cleansing fluid supply means which does not require the sampler to leave the sampling position so as to draw rinse fluid from a second receptacle. It also does not require a receptacle with in-flow and out-flow as a source of rinse fluid.

In this invention, the sample may be brought to the probe or the probe may be lowered into the sample container. After a sample is removed from a container through the probe and conduit, a surge of cleansing fluid is introduced from a remote reservoir into the conduit at a point rearwardly from the probe so that a part of the rinse fluid flows downstream through the conduit behind the sample, cleansing the conduit behind the sample. Another part of the cleansing fluid move forwardly toward the probe (in the reverse direction that the sample had been drawn, i.e.: upstream). Such cleansing fluid is then discharged through the probe and this may be done directly into the sample container from which the sample was just removed, or, if preferred, into a sump or reservoir.

The container may also be designed in such a way that when the cleansing fluid is discharged through the probe into the container, the flush of cleansing fluid removes any sample remaining in the container and not only flushes the inner portion of the probe but also cleanses the outside of the probe as the cleansing fluid takes the place of the sample in the container. The probe may be perforated to assist external rinsing.

The cleansing fluid enters the stream beyond the probe at any remote reservoir convenient location and is supplied from any source capable of surpassing in pressure the latent back pressure in the line at the point of connection (which may be a T or Y valve or other stream insertion means). The cleansing fluid is provided in such volume at the point of connection that it can fill both the line leading from the valve to the probe and the line leading downstream from the valve, either in equal proportions or in unequal proportions, as preferred, for the kind of operation being carried out, e.g., water sampling, blood sampling, oil sampling, gas sampling or the like.

The cleansing fluid may be segmented with other fluids to enhance the cleansing action or to separate adjacent dissimilar substances.

The cleansing fluid is supplied after sample withdrawal of a selected volume, but is not supplied during the actual sample withdrawal process. This is prevented by any means capable of furnishing a valving or on-off action, ranging from pinching shut a flexible tubing, or any of the known valve systems such as a gate or rotary member moved mechanically, or by another form of energy such as electricity or gas pressure. The cleansing fluid may also be prevented from entering the system by temporary application of a partial vacuum to its source.

Thus the liquid sample supply apparatus of the present invention is found to be relatively simple and uncomplicated, providing a foolproof and inexpensive means of withdrawing liquid samples for test purposes.

The principal object of the present invention is to provide a sample supply apparatus where the flushing of the probe and conduit is done by a "backwash" of cleaning fluid through the conduit and probe without interfering with the forward flow of the sample, fluid segments and rinse fluid.

Another object of the present invention is to provide a sample supply apparatus wherein the sampling and the cleansing of the sample probe may be done in a single container or into a sump either filled or empty or rinse fluid.

Another object of the present invention is to provide a liquid sample supply apparatus wherein the cleansing fluid is introduced into the sample takeoff conduit downstream from the probe so that the cleansing fluid may flow in two directions through the conduit, thus cleaning the conduit behind the liquid sample and also cleaning the probe by a counterflow outwardly through end of the probe or through perforations along its extremity.

Still another object of the present invention is to provide a sample supply apparatus which does not require a separate cleansing bath in order to rinse the probe and sample conduit.

With the above and other objects in view, more information and a better understanding of the present invention may be achieved by a reference to the following detailed description.

DETAILED DESCRIPTION

For the purpose of illustrating the invention, there is shown in the accompanying drawing a form thereof which is at present preferred, although it is to be understood that the various instrumentalities of which the invention consists can be variously arranged and organized, and that the invention is not limited to the precise arrangements and organizations of the instrumentalities as herein shown and described.

In the drawings wherein like reference characters indicate like reference parts:

Sample supply devices of the present invention are generally used in motor-driven circular trays which automatically and sequentially advance a plurality of cups or containers, each filled with fluid to be sampled and tested. Descriptions of such sample devices have been shown in the patents referred to above.

Figure 1:
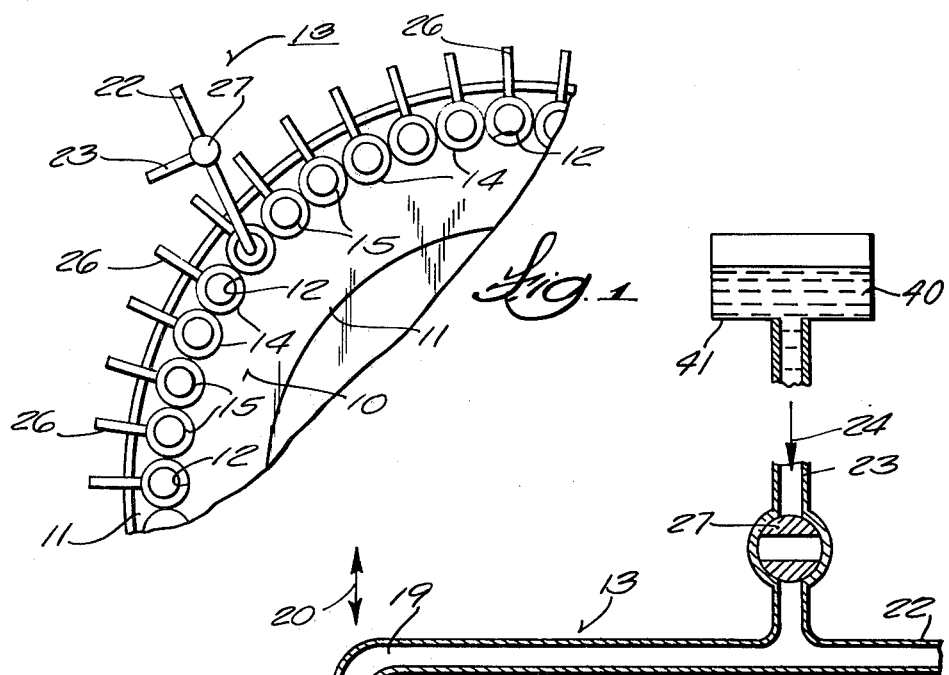
FIG. 1 represents a fragmentary top plan view of a sample tray and takeoff device according to the present invention.

In FIG. 1, a fragmentary plan view of such tray is shown at 10. This tray may be circular and motor-driven so that the cup-carrying portion 11, with a series of holes 12 therein, is moved beneath the sample takeoff device 13.

The tray 11 has a liquid container or cup 14 supported in as many of the holes 12 as there are samples to be tested. These cups will be described subsequently but generally contain a sample of the fluid to be tested and to be removed by the takeoff device 13.

Figure 2:
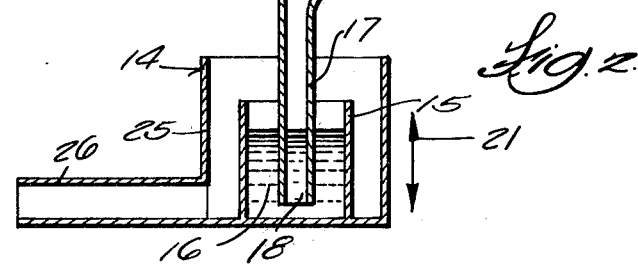
FIG. 2 represents a vertical cross-sectional view, fragmentary in nature, illustrating the relationship of probe and container.

As shown in FIG. 2, the cups 14 include at least an inner element 15 which contains the fluid 16 to be sampled. The takeoff device 13 includes a probe 17, the end 18 of which is disposed in the container 15 when the fluid 16 is to be removed through the conduit 19.

It is obvious that in order for the tip 18 of the probe 17 to be disposed within the cup 15, the cup and the probe must be relatively movable and thus I have shown arrow 20 as an indication that the probe may move up and down, and arrow 21 to indicate that the cup may move up and down. It is not material to the invention whether the probe moves downwardly into the cup or whether the cup moves up around the probe, as long as during the sampling operation the tip 18 is disposed within the cup 15 at the time when the sample is being removed.

The takeoff conduit 19 extends away from the probe 17, as at 22, and may be connected or otherwise suitably arranged so that the sample will be conducted to the rest of the testing apparatus (not shown).

Disposed along the conduit 19 is a secondary conduit 23 through which cleansing fluid 40 may be supplied from a container or reservoir 41 in the direction indicated by the arrow 24.

I also show in FIG. 2 that the container 15 has suitably arranged therewith an auxiliary container 25 and discharge outlet 26 so that the overflow of any fluid (sample or cleansing fluid) from the container 15 may be carried away through the discharge pipe 26 to a remote sump (not shown).

Disposed within the conduits 19 and 23 and more preferably at the junction thereof, is a valve 27 which controls the flow of fluid through the conduits 19 and 23.

Figure 3:
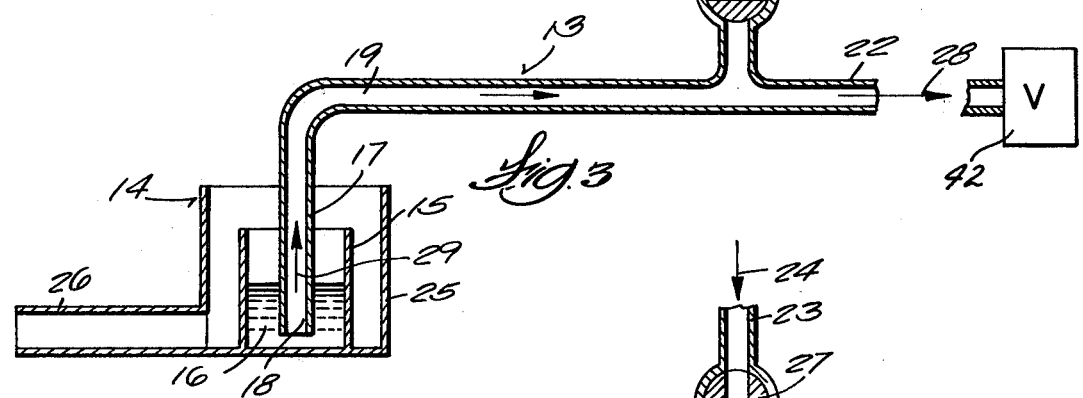
FIG. 3 is a fragmentary vertical schematic view illustrating the disposition of the parts when a sample is being removed from the container by the probe.
Figure 4:
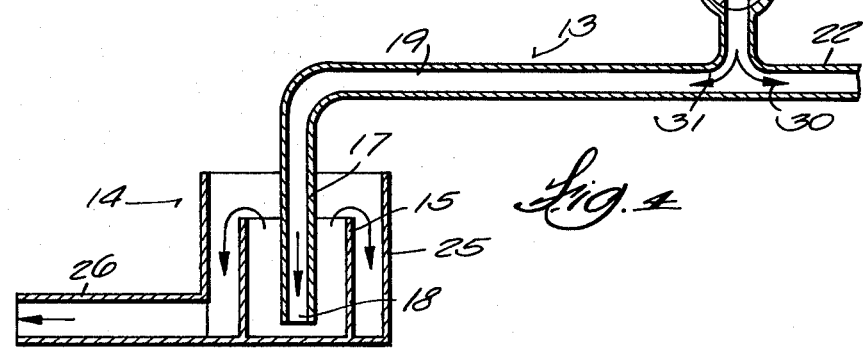
FIG. 4 is a schematic view similar to that of FIG. 3 showing the disposition of the elements when the cleansing fluid is flowing into a sample cup which also serves as a cleansing fluid sump.

Referring now to FIG. 3, I indicate that the valve 27 may be closed when a vacuum is drawn in the line 19 by a vacuum source 42 so that any fluid 16 therein will move through the probe 17 and in the direction of the arrow 29 and through the conduit 19 in the direction of the arrow 28. Such withdrawal of the sample will continue until a sufficient sample has moved through the portion 22 of the conduit 19 downstream beyond the valve 27.

When a sufficient supply of the sample to be tested is moved beyond the valve 27, the valve is operated and a supply of cleansing fluid 40 is introduced from the reservoir 41 through the conduit 23 through the valve 27 in the direction of the arrow 24, passing the valve 23, so that a portion of the cleansing fluid 40 flows downstream in the direction of the arrow 30, filling the conduit 19 behind the sample just removed through such conduit and avoiding the entrapment of any bubbles.

An additional portion of the cleansing fluid passes through said conduit 19 in a counterflow direction as indicated by the arrow 31, moving from the valve 27 "upstream" through the conduit 19 and discharging through the probe 17 into the container 15. Thus it not only flushes the forward end of the conduit 19 and the probe 17 but also flushes the unused portion of unwanted sample out of the container 15, filling the container 15 with cleansing fluid, and thus cleaning the exterior of the probe 17 which lies within the container 15.

The unwanted sample fluid 16 and the excess cleansing fluid 40 overflow the top of the container 15 into the container 25 and out through the discharge pipe 26 into the waste sump.

It is obvious that the valve 27 may be controlled in such a way that the flow of fluid 40 through the conduit 19 may be stopped. Thus, when the probe and the cups are separated, there will not be an excess of cleansing fluid 40 discharging from the probe with no container to receive it.

It is also obvious that the cleansing fluid 40 may be discharged into a separate cup held in the next succeeding hole in the tray 11 so that the cleansing and discharge may be done without contaminating the unused portion of the sample left behind in the cup after the sample to be tested has been removed.

It is also obvious that the probe and conduit may be made to pivot about a vertical axis so that when the probe and cup are separated and the probe is vertically above the cup, it may be pivoted horizontally out of alignment with the cup, and the cleansing fluid 40 may be discharged into a sump placed adjacent the sample tray rather than in line with the cups in sample tray.

The advantages of the system of sequential cleaning of probe and lines, without the use of a separate receptacle are:

(1) Fewer restrictions in the probe movement avoiding sequential repositioning or tilting in multiple planes.
(2) Better flushing of the probe by the use of a reverse flow to wash out retained sample segments.
(3) Simultaneous washing of the probe and processing lines without interruption using reverse flow to the probe and uni-directional flow following the sample, with or without separation by a segment of another fluid.
(4) Avoiding the use of a separate receptacle with continuously flowing wash fluid (which is wasteful) and which requires the use of weirs or overflow baffles and allows the surface of the fluid to be exposed to ambient environmental conditions that contaminate the wash fluid and give inaccurate analytical results.
(5) The wash supply source can be remote and does not need to be in a fixed position with respect to the probe and, in fact, can be moved while sampling or washing are in process.
(6) Sampling can be done from a sealed container with rinsing done back into the container, if desired, or rinsing may be into a separate container accessible by sequential movement of the probe from the sample position to a rinse position. In this position is required only an empty receptacle, drain, sump, or a container with cleaning fluid can be used, accepting the discharge of wash fluid while the probe is immersed, if desired.

It is to be understood that the present invention may be embodied in other specific forms without departing from the spirit or special attributes hereof, and it is, therefore, desired that the present embodiment be considered in all respects as illustrative, and, therefore, not restrictive, reference being made to the appended claims rather than to the foregoing description to indicate the scope of the invention.

Having thus described my invention what I claim as new and desire to protect by Letters Patent are the following:

1. A supply device for liquid analysis including,
a probe,
a liquid container,
said probe and said liquid container being relatively movable whereby said probe may be selectively disposed in said liquid container,
a takeoff conduit connected to the probe for conveying liquid from the liquid container,
a rinse fluid reservoir,
rinse fluid in said reservoir,
a movable valve in the takeoff conduit,
a secondary conduit connecting the reservoir and the valve,
vacuum means for drawing liquid from said liquid container through said probe and takeoff conduit when said valve is in a first position,
said rinse fluid flowing from said reservoir through said secondary conduit into the takeoff conduit when said valve is in a second position,
a portion of said rinse fluid flowing downstream from said valve toward said vacuum means and a portion of said rinse fluid flowing upstream from said valve toward and through said probe and into said liquid container when said valve is in said second position.

* * * * *